United States Patent
Stille et al.

(10) Patent No.: US 9,980,695 B2
(45) Date of Patent: May 29, 2018

(54) METHOD AND APPARATUS FOR REDUCING ARTEFACTS IN COMPUTED TOMOGRAPHY IMAGES

(71) Applicant: UNIVERSITÄT ZU LÜBECK INSTITUT FÜR MEDIZINTECHNIK, Lübeck (DE)

(72) Inventors: Maik Stille, Luebeck (DE); Thorsten M. Buzug, Gross Sarau (DE)

(73) Assignee: UNIVERSITAET ZU LUEBECK INSTITUT FUER MEDIZINTECHNIK, Luebeck (DE)

( * ) Notice: Subject to any disclaimer, the term of this patent is extended or adjusted under 35 U.S.C. 154(b) by 1 day.

(21) Appl. No.: 15/310,368

(22) PCT Filed: May 12, 2015

(86) PCT No.: PCT/EP2015/060493
§ 371 (c)(1),
(2) Date: Nov. 10, 2016

(87) PCT Pub. No.: WO2015/173251
PCT Pub. Date: Nov. 19, 2015

(65) Prior Publication Data
US 2017/0150937 A1    Jun. 1, 2017

(30) Foreign Application Priority Data
May 14, 2014  (DE) .................. 10 2014 007 095

(51) Int. Cl.
*G06K 9/00*  (2006.01)
*A61B 6/00*  (2006.01)
(Continued)

(52) U.S. Cl.
CPC ............ *A61B 6/5258* (2013.01); *A61B 6/032* (2013.01); *A61B 6/12* (2013.01); *A61B 6/5205* (2013.01);
(Continued)

(58) Field of Classification Search
CPC .................................. A61B 6/00; G06T 11/00
(Continued)

(56) References Cited

U.S. PATENT DOCUMENTS

| | | | |
|---|---|---|---|
| 8,233,586 B1* | 7/2012 | Boas | ................. G06T 5/002 378/207 |
| 9,495,770 B2* | 11/2016 | Noo | ................. G06T 11/003 |
| 2008/0273651 A1 | 11/2008 | Boas | |

FOREIGN PATENT DOCUMENTS

DE   10 2012 212 774 A1   1/2014

OTHER PUBLICATIONS

International Search Report prepared by the European Patent Office dated Aug. 4, 2015, for International Application No. PCT/EP2015/060493.

(Continued)

*Primary Examiner* — Abolfazl Tabatabai
(74) *Attorney, Agent, or Firm* — Sheridan Ross P.C.

(57) ABSTRACT

The invention relates to a method and an apparatus for reducing artefacts that are caused particularly by disturbance bodies and/or metal bodies in computed tomography (CT) images by means of a regulated iteration process that can be integrated particularly into a process for processing measurement data and preferably into a superordinate process for data alignment.

5 Claims, 3 Drawing Sheets

Figure 1:
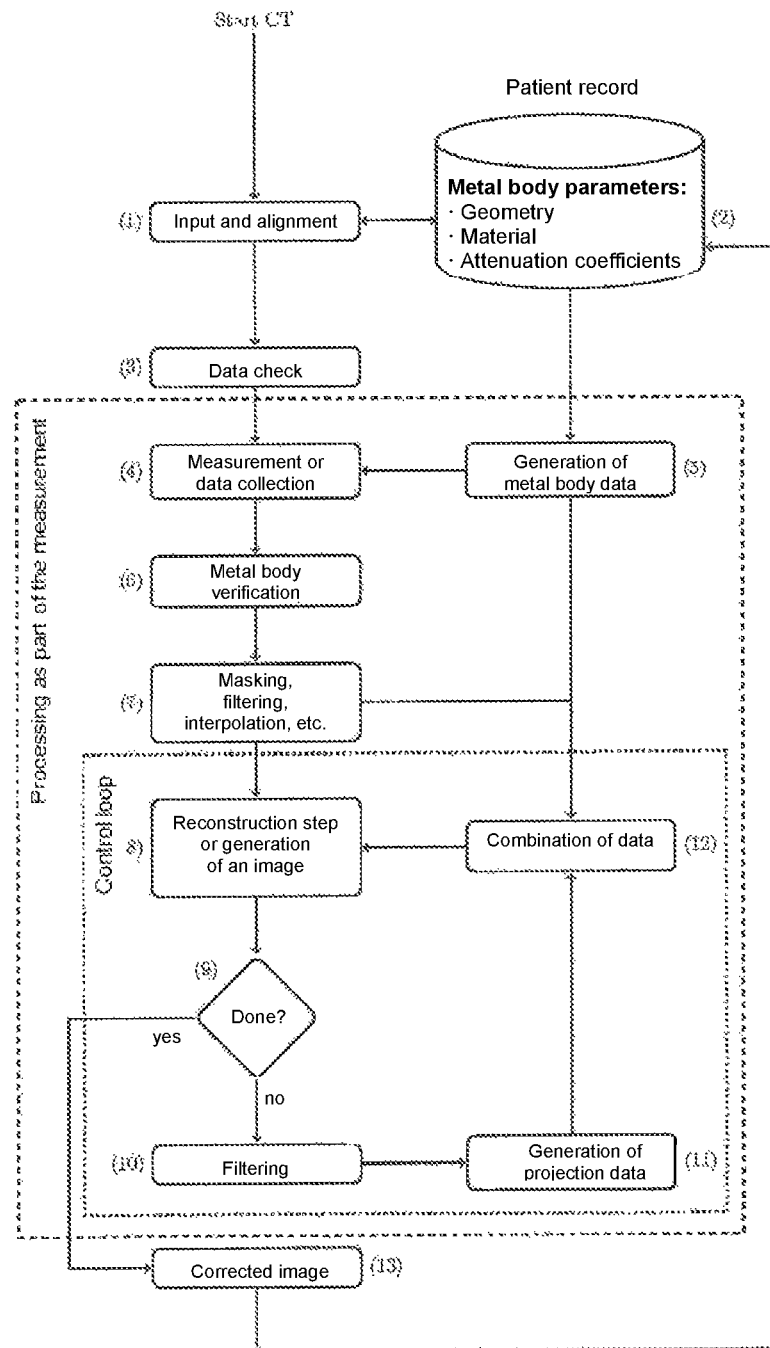

(51) Int. Cl.
　　　*G06T 11/00*　　　(2006.01)
　　　*A61B 6/03*　　　(2006.01)
　　　*A61B 6/12*　　　(2006.01)

(52) U.S. Cl.
　　　CPC .......... *G06T 11/005* (2013.01); *G06T 11/006* (2013.01); *G06T 2207/10081* (2013.01); *G06T 2211/424* (2013.01)

(58) Field of Classification Search
　　　USPC ....... 382/128, 129, 130, 131, 132, 133, 134; 378/4, 8, 21–27, 901
　　　See application file for complete search history.

(56) References Cited

OTHER PUBLICATIONS

Webster Stayman J et al: "Likelihood-based CT Reconstruction of Objects Containing Known Components", 11th International Meeting on Fully Three-Dimensional Image Reconstruct! on In-Radiology and Nuclear Medicine, Jul. 11 Jul. 15, 2011, Potsdam, Germany, Jul. 11, 2011, pp. 254-257.

Search Report prepared by the German Patent Office dated Jan. 15, 2015, for German Application No. 10 2014 007 095.6.

\* cited by examiner

US 9,980,695 B2

METHOD AND APPARATUS FOR REDUCING ARTEFACTS IN COMPUTED TOMOGRAPHY IMAGES

CROSS REFERENCE TO RELATED APPLICATIONS

This application is a national stage application under 35 U.S.C. 371 and claims the benefit of PCT Application No. PCT/EP2015/060493 having an international filing date of 12 May 2015, which designated the United States, which PCT application claimed the benefit of German Patent Application No. 10 2014 007 095.6 filed 14 May 2014, the disclosure of each of which are incorporated herein by reference in their entireties.

The invention relates to a method as well as an apparatus for reducing artefacts in computed tomography (CT) images caused particularly by obstructive bodies and/or metal bodies in accordance with the respective precharacterizing part of the independent claims.

Computer tomography (CT) represents a considerable advancement over conventional radiography. CT imaging is based on the varying attenuation of X-rays through an object, wherein cross-sectional views are produced by computer-based evaluation of a plurality of X-rays of the object taken from different directions. The imaging process is fast and the resolution is better, as is the orientation and positioning of bodies, than is the case in conventional radiography which only returns a projected image of the respectively examined object in one plane. With computed tomography, it is thus in particular possible to obtain a three-dimensional representation of vascular and skeletal structures of high isotropic spatial resolution. Computed tomography is therefore one of the most important imaging techniques in daily clinical practice.

One problem the CT procedure faces is metal bodies in the object to be examined which greatly interfere with the imaging process and produce artefacts in the CT image.

For example, dental fillings and implants have very high X-ray attenuation coefficients. As of a certain metal thickness or given edges and complex geometry to an obstructive body, there can be such a high absorption of the X-ray as to thereby so greatly attenuate the useful signal that it drops below the so-called noise threshold and thus no longer suffices in differentiating the object.

So-called beam-hardening artefacts represent a further interference. Since radiation absorption of objects is dependent on the energy and low-energy rays are more greatly absorbed than high-energy rays, this leads to an increase of the average energy for the entire X-ray spectrum. This occurs in all types of tissue but is many times higher in the presence of metals and leads to the corresponding defects in the CT images.

In the projections of a computed tomography image, the resulting metal artefacts appear as interferences from a combination of the cited physical effects subject to the material and the geometrical structure of metal objects in the object being examined. The resultant artefacts compromise the informational content of the reconstructed CT image up to the point of the relevant information being partially or even completely lost and thus rendering a subsequent diagnostic interpretation of the data impossible.

The task which the invention addresses is that of specifying a method as well as a corresponding apparatus for easily and reliably reducing artefacts in CT images.

This task is solved by the method and the apparatus according to the independent claims.

The inventive method for reducing artefacts in computed tomography (CT) images which are caused particularly by obstructive bodies and/or metal bodies is characterized by the following sequence of steps being performed in at least one iteration process:

(a) reconstructing or generating CT image data from first projection data,
(b) querying one or more limiting values and/or terminating conditions of the iteration process and, in the case of the limiting values being reached and/or the terminating conditions being met, aborting the iteration process and outputting the CT image data, otherwise continuing the iteration process with step (c),
(c) reducing artefacts in the reconstructed/generated CT image data by filtering the CT image data,
(d) generating second projection data from the filtered CT image data,
(e) combining the first and second projection data, in particular replacing the first projection data by the second projection data in due consideration of the obstructive body data and transferring the projection data thereby obtained to step (a) as the first projection data.

The inventive apparatus for reducing artefacts in computed tomography (CT) images which are caused particularly by obstructive bodies and/or metal bodies is characterized by at least one iterative control loop configured to perform the following sequence of steps:

(a) reconstructing or generating CT image data from first projection data,
(b) querying one or more limiting values and/or terminating conditions of the iteration process and, in the case of the limiting values being reached and/or the terminating conditions being met, aborting the iteration process and outputting the CT image data, otherwise continuing the iteration process with step (c),
(c) reducing artefacts in the reconstructed/generated CT image data by filtering the CT image data,
(d) generating second projection data from the filtered CT image data,
(e) combining the first and second projection data, in particular replacing the first projection data by the second projection data in due consideration of the obstructive body data and transferring the projection data thereby obtained to step (a) as the first projection data.

The invention is based on the approach of being able to use information about the form and/or composition of an obstructive body in the object to be examined to inhibit or at least reduce artefacts in the reconstructed image and thus improve the degree of detail to the CT image. In addition, CT images of the object to be examined that can contain both known as well as unknown obstructive bodies of metallic or partly metallic materials are reconstructed in an iteration process and/or an iterative control loop taking into account information stored on the obstructive body or bodies by in particular selectively eliminating or at least reducing the data impacted by the obstructive body or bodies. The inventive method, inventive apparatus respectively, thus comprises an iterative reconstruction approach in which prior knowledge in the form of additional constraints is incorporated into the reduction of metal artefacts.

Preferably, the type of implants and material used in their manufacture is known, recorded or sufficiently documented and stored in a database. Implants already within the body of a patient are preferably recorded in a patient record, able to be physically parameterized and aligned, and retrievable at any time. This information is preferably parameterized as physically unique variables such as, for example, attenuation coefficients which informatively reflect particularly the chemical composition and the geometrical form of the implant and can be factored into the inventive reconstruction method so as to reduce and/or completely nullify the influence of the metal artefacts.

On the whole, the invention reduces artefacts in CT images in a simple and reliable manner.

In the context of the invention, the term "projections" is to be understood as multiple, particularly a plurality of absorption profiles of the object from different directions. Correspondingly, the term "projection data" is to be understood as the data from projections characterizing the absorption behavior of the object in different directions.

Furthermore, the terms "image" and "CT image" in the context of the invention refer to multiple, particularly a plurality of sectional or volumetric representations of objects reconstructed from projections and/or a corresponding two- or three-dimensional image data record in which the information correlates to pixels or voxels.

Preferential embodiments of the invention make use of one or more of the following methods: filtering of intermediate artefact reduction results; dynamic weighting of additional constraints in an iterative control loop; correcting for inconsistencies in the radon room; introducing known obstructive metal body geometries into the reconstruction process; introducing known metallic obstructive body attenuation coefficients into the reconstruction process.

One or more of the above-cited methods allow the highest density of information to be generated from CT measurements and known patient data and the visualizing of same for the user, in particular a physician. Furthermore achieved is being able to introduce prior technical knowledge on implants and their known technical parametric properties into the metal artefact reduction (MAR). It is also possible to differentiate and analyze the formation of new artefacts by interpolation errors in known MAR approaches and integrate same into the inventive method. Last but not least, it is possible to minimize residual artefacts during the reconstruction.

In one particularly preferential embodiment of the invention, the at least one iteration process is integrated into a further process having the following steps:

(f) generating the obstructive body data, particularly obstructive body projection data, on the basis of the obstructive body-characterizing parameters stored in particular in a database,
(g) collecting/acquiring first projection data and parameterizing said first projection data,
(h) verifying whether an obstructive body is present in the object based on the first projection data,
(i) processing, in particular masking and/or filtering and/or interpolating the first projection data and transferring the processed first projection data to step (a) and (f).

In the further module, procedural steps for processing the data collected as part of the measurement are verified and processed. The independent module of the inventive iteration process or iterative control loop respectively can thereby be integrated into the further module; i.e. all the interfaces and parameter transfers are uniquely definable and thus non-proprietary; i.e. the interfaces or respectively the parameters to be transferred follow international standards and norms from the data and measured variable perspective and are thus also easily implementable in existing standardized methods.

In a further preferential embodiment of the invention, the at least one iteration process is integrated, in particular together with the further process, into a superordinate process having the following steps:

(j) starting the method,
(k) inputting of data, particularly patient-related data,
(l) retrieving parameters characterizing an obstructive body and/or data identifying an obstructive body from a database, in particular an electronic patient record, on the basis of the entered data,
(m) transferring the retrieved parameters/data to step (f) and/or step (g), in particular subsequent verification and, if applicable, supplementation and/or correction of the parameters/data.

An input with data alignment to the database-supported parameterized data and the aligning and archiving of the procedural result is effected in the superordinate module. The superordinate module can thereby also be integrated into the further module and independent module of the inventive iteration process or iterative control loop respectively. That as stated in connection with the further module applies analogously to the interfaces and parameter transfers.

The multilayer structure to the method and/or apparatus of different modules in the form of a parameterized iterative control loop, a further module for processing data collected as part of the measurement and a superordinate module which substantially links the data input and/or output to a database, allows the data-related adaptation of further processes into the respective modules without disrupting the systematic structure to the method and/or the apparatus.

The following will make use of an example to illustrate further preferential aspects of the method and/or apparatus for reducing artefacts.

After identifying a patient having the name of "First name, Last name" and the date of birth of "Apr. 1, 1979," so-called personal data available as metadata, it is preferably first ascertained on the basis of an electronic patient record that this patient has had a metal pin implanted in the lower thigh. The metal pin has a model number of "N123456," by means of which information on the implanted pin as to its form, e.g. length and diameter, its composition, e.g. titanium, as well as its attenuation coefficients can be retrieved from the patient record or by linking to another database.

A CT scan of the patient thereafter follows in which a plurality of first projections are taken of the patient's lower thigh which depict the absorption behavior of the material penetrating the lower thigh along the different directions of projection.

Prior to, during or after the CT scan, obstructive body data in the form of a model of the metal pin is generated from the data characterizing the metal pin.

A verification preferably follows the CT scan to determine which projections of the CT scan contain the metal pin. Projections in which the metal pin is detected are removed and/or corrected in a first correction step, for example by interpolation, filtering or masking.

The first projection data obtained in this first correction step is provided to an iteration process and/or an iterative control loop in which in which CT image data, particularly sectional or volumetric images, of the lower thigh is initially generated from the first projection data, for example by simple backprojection or so-called filtered backprojection.

It is thereafter preferably checked whether the CT image data generated conforms to predefined limiting values and/or terminating conditions of the iteration process. This can for example occur on the basis of the gradients of a target function or a so-called log-likelihood function for a transmission CT.

If so, the iteration process is aborted and output of the CT image data follows in the form of an artefact-free or at least artefact-reduced image of the lower thigh which is preferably added to the electronic patient record of patient "First name, Last name" or can additionally supplement the existing data records respectively.

If not, the iteration process is continued by the artefacts caused by the metal pin being reduced in the reconstructed or generated CT image data by filtering the CT image data. Filtering is effected for example by means of bilateral filters, with which the CT images are filtered with respect to grey tones and distances separating the individual pixels or voxels, or by means of a diffuser such as e.g. a Gaussian filter or a median filter. The artefacts caused by the metal pin are thereby reduced while at the same time the relevant anatomical structures of the lower thigh are preserved.

In a further step, second projection data is generated from the filtered CT image data. Preferably, one of the above-described projection methods analogous to CT image data reconstruction from the first projection data of the lower thigh is hereby used so that the first and second projection data are compatible.

In a subsequent step, the first projection data obtained from the CT scan of the lower thigh and subsequently subjected to a first correction is combined with the second projection data, by in particular some of the first projection data being replaced by second projection data subject to the obstructive body data in the form of the model of the metal pin. Preferably, first projection data able to be associated with the metal pin is thereby removed and replaced by corresponding second projection data.

The combined projection data thereby obtained is then reintroduced back into the first step of the iteration process as first projection data, with CT image data, particularly sectional or volumetric images of the lower thigh, then being able to be generated from the first projection data.

The iteration process preferably continues until the respectively most current generated CT image data—as already described above—satisfies the predefined iteration process limiting values or terminating conditions and an artefact-free or at least artefact-reduced CT image of the lower thigh is output.

Figure 2:
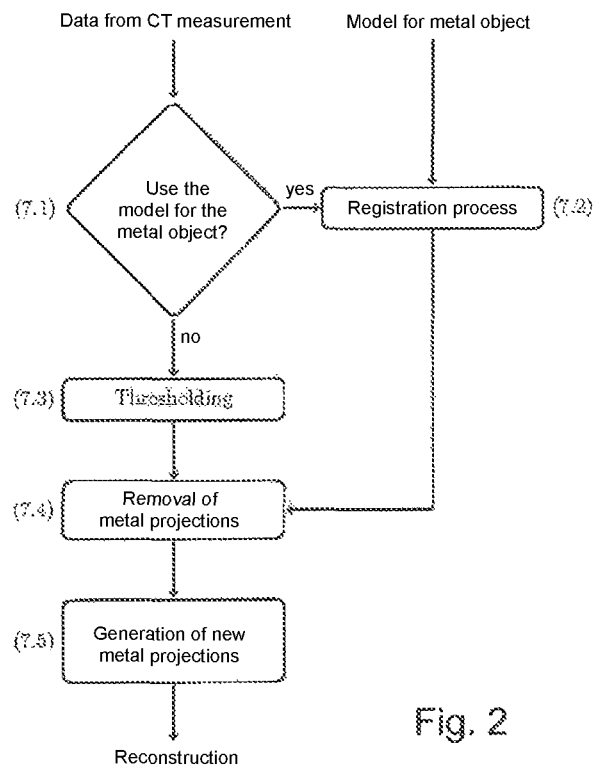
Figure 3:
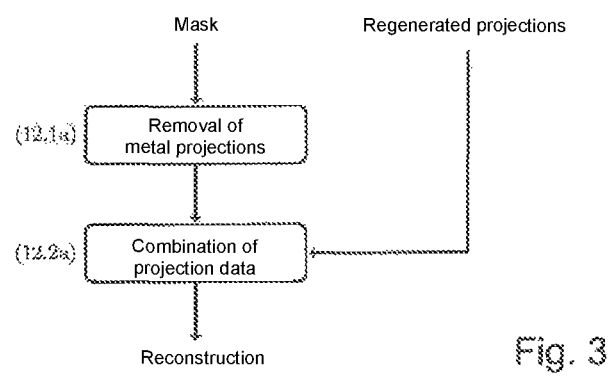
Figure 4:
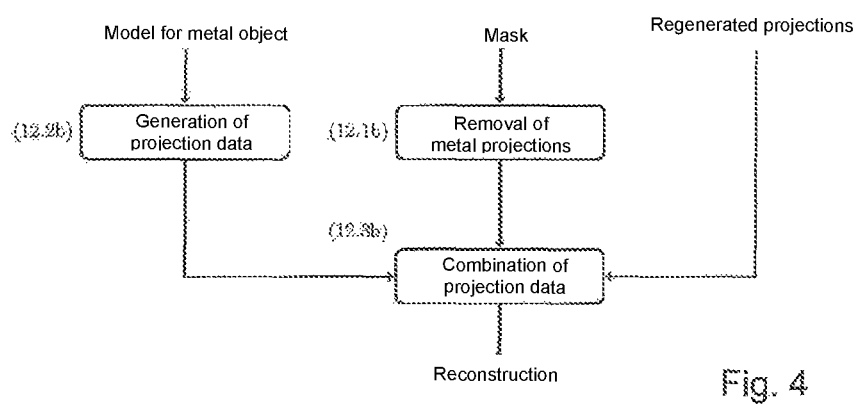

Further advantages, features and possible applications of the present invention will follow from the description below in conjunction with the figures. Shown are:

FIG. 1 a flow chart of a method for reducing artefacts in computed tomography (CT) images caused particularly by obstructive bodies and/or metal bodies by means of a regulated iteration process integrated into a process for processing measurement data and a superordinate data alignment process;

FIG. 2 a microstructure of procedural steps from the flow chart of FIG. 1 of a method for reducing artefacts in computed tomography (CT) images caused particularly by obstructive bodies and/or metal bodies which shows a possible process for processing measurement data;

FIG. 3 a microstructure of procedural steps from the flow chart of FIG. 1 of a method for reducing artefacts in computed tomography (CT) images caused particularly by obstructive bodies and/or metal bodies which shows a possible first process for combining data; and FIG. 4 a microstructure of procedural steps from the flow chart of FIG. 1 of a method for reducing artefacts in computed tomography (CT) images caused particularly by obstructive bodies and/or metal bodies which shows a possible second process for combining data.

FIG. 1 shows a flow chart of a method for reducing artefacts in computed tomography (CT) images caused particularly by obstructive bodies and/or metal bodies by means of a regulated iteration process (dotted box) which is or can be integrated into a further process for processing measurement data (dashed box) and into a superordinate data alignment process. The method, or the corresponding apparatus respectively, is hereby subdivided into three modules. The first module encompasses four elements (1), (2), (3) and (13) comprising the data input, data management and data output. The second module comprises processing within the scope of the CT measurement with the elements (4) to (7) and the third control loop module (elements (8) to (12)) in which automated iterative image processing optimization occurs.

The input and alignment of relevant data occurs in the first element (1) of the flow chart. Input includes personal data such as, for example, the name and the date of birth serving for identification purposes. This is followed by an aligning or respectively accessing of data from an electronic patient record or the generating of an electronic patient record (2).

The electronic patient record (2) contains for example at least information on the patient's age, medical condition, prescribed medicines, length of hospitalization and preferably information on existing implants, particularly metal implants.

Should there be a metal implant, the model number of the implant can for example be retrieved from the record. This number enables for example the obtaining and providing of information on the form and/or composition of the implant and the supplementing and/or correcting of the third Data check (3) element.

The second module encompasses the processing of the data as part of the measurement. To this end, the fourth element comprises measurement or data collection (4) respectively when performing the actual CT scan. This usually entails irradiating the patient once and collecting raw data, in particular a plurality of projections reflecting the absorption behavior of the object in different directions. Parallel to this, the metal body data (5) is generated subject to or on the basis of information from the patient records. Preferably generated here is a model of the given metal implants inside the patient. This model is then further used to reduce any appearing artefacts. In particular, this model contains information on the geometry of an implant, on its chemical composition and on the attenuation coefficients resulting therefrom.

A metal body verification (6) ensues in the sixth element. Based on the data obtained from element (4), it can thereby be determined whether or not there is a metal body present within the patient. In particular, this can be performed on each layer and/or projection of the realized CT scan. No metal artefact correction or reduction is needed with layers/projections not containing any metal objects. Should a metal object be present, the proposed methodology continues further.

A metal artefact correction or reduction (MAR) then follows in the seventh element by masking, filtering, interpolation, etc. (7), whereby a removing or processing respectively of projections running through metal is obtained. Different methods can hereby be used such as, for example: linear interpolation, quadratic or cubic interpolation, B-spline interpolation or other interpolation methods, correction methods based on inpainting, or normalized metal artefact reduction.

The third module is embedded within the second module and designed as an independent, in particular iterative, control loop. The reconstruction step (8) ensues in this control loop in the eighth element. The first time this element is reached, a first image is generated from the collected data. This is usually still far removed from the corrected result in element (13).

The following methods are preferential when generating the image based on the raw data.

A simple backprojection can be used in the case of one iterative formula. This for example involves a line-driven or even raycasting projection method.

An analytical method such as for example filtered back-projection already generates a completely reconstructed image after a first iteration. However, the image can still contain artefacts unable to be rectified until being run through the control loop multiple times.

A termination query (9) in the ninth element determines whether the reconstruction criteria are fulfilled based on predefined values and the reconstruction can be terminated. This can for example ensue on the basis of a target function's gradients. In the case of a statistical reconstruction, this can be log-likelihood function for a transmission CT. Furthermore, a dependency in terms of already known prior knowledge can be integrated and the predefined values from input (1) taken into consideration. It can hereby for example also be checked how precisely the previously known attenuation coefficients mesh into the reconstructed image. If the predefined terminating criteria are met, the method is then successfully concluded and a finished artefact-corrected image is output, as illustrated by the thirteenth element (13).

Should, on the other hand, the criteria not be met, a filtering (10) is then performed in the tenth element of the control loop. In this process, the current reconstructed image from element (8) is modified with image filters, e.g. bilateral filters. The image is hereby filtered in terms of the grey tones and the distances between the individual pixels/voxels. Other filtering possibilities are offered by diffusers such as e.g. Gaussian filters or median filters. The control loop is thereby parameterized in such a manner that artefacts are reduced while the patient's anatomical structures are preserved.

Projection data (11) is generated in the eleventh element. So that the projection data will be compatible, the same projection method is used to generate new projection data as in the eighth element (8). The generating of projection data simulates the behavior of the CT machine performing the measurement in the fourth element (4). Accordingly, in generating the projection data, the patent is not subjected to repeated X-rays but rather the current reconstructed image is used to simulate the course of rays. The generated projection data is further processed in the twelfth element (12) by a combining of data (12). Here, the projection data generated with the element (7) methodology is replaced by the projection data generated in element (11). The mask which was used in element (7) can likewise be used here. Projections associated with the metal object are first removed and replaced by the projections generated in element (11). A combination of the projections resulting from element (7) and (11) is thereby possible.

The control loop is exited in the thirteenth element and a corrected image (13) is generated or output respectively as the method result. The method generates an artefact-free or at least artefact-reduced image as a reconstruction which is thereafter added to the electronic patient record (2) in order to improve the density of information.

FIG. 2 shows an example method for configuring the seventh element (7) from FIG. 1, particularly for selective masking, filtering and interpolation.

In element (7.1), a database query determines whether there is a parameterized model for the metal object from the CT measurement and whether it should be used. The criteria for this decision are stored in the database. If a model of the metal object is stored in the database for masking/segmentation and can thus be retrieved parameterized, this is then verified by a registration step (7.2), the registration "Find the correct position of the metal object in the image" problem solved, and an exact segmentation of the metal object made. This segmentation can occur with each further run through the control loop and can thus be refined by iteration.

A case differentiation applies in the further processing of the method steps.

If the identified model for the metal object is not to be used, for example to avoid additional runtime through the registration process, the classification of metal in the image must then be resolved by another process in the Thresholding (7.3) element. An example of such an approach with this element is a so-called threshold segmentation. Here, a predetermined threshold for the parameterizing of metals is established which divides the image into two sections based on the "metal" and "non-metal" criteria.

A segmenting of the metal object thereby occurs in element (7.4), "Removal of metal projections," i.e. projections or X-rays respectively, through which metal extends. All the projection data having data associated with the specific metal object is removed from the originally measured data. Unspecified data, with which for example no differentiation was made as to a segmentation in the raw data collection or in the image field is subject here to a further parameterized case differentiation. Should the classification have been made in the image field, a projection of the resulting mask for the metal object must then be executed in the raw data collection.

In the case of a classification of projections into metal projections and non-metal projections, the projections associated with metal can be removed from the raw data collection or from the measured data respectively.

Removing the metal projections results in a gap in the raw data collection or measured data respectively. This means that information which is needed to reconstruct an image is missing. One possibility is realizing the reconstruction under exclusion of the metal projections. This produces image artefacts to be corrected. Another possibility lies in realizing an initial metal artefact reduction. The resultant gap in the element (7.5) is thereby replaced by newly generated metal projections. In the simplest case, these could result for example from a linear interpolation. It should be noted that this step is highly variable and a plurality of methods can be used.

FIGS. 3 and 4 show possible methods for regulating the twelfth element (12) from FIG. 1 for the combination of data.

FIG. 3 illustrates a first control step variant for element (12) of the FIG. 1 method. The "Removal of metal projections" element (12.1*a*) removes the metal projections from the measured data using the mask formed or used in element (7). Should the criteria for the projection data be met in element (12.2*a*), the element (12.2*a*) data is buffered.

The projection data through the metal object generated from the "Generation of projection data" element (11) is combined with the measured projection data in the "Combination of projection data" element (12.2*a*). The result thereby consists of the projections measured in element (4), which are associated with the patient's anatomy, and the projections artificially generated in element (11).

The new metal projections consist for example of a weighted combination of projections originally measured in element (4), generated in element (7) and obtained in element (11). It is thereby also possible to use only the projections resulting from element (11).

FIG. 4 illustrates a control step variant for element (12) of the FIG. 1 method. The metal projections are first removed from the measured data in element (12.1b) using the mask from element (7). If the criteria for the projection data is met in element (12.2b), the element (12.2b) data is buffered. Using the model for the metal implant generated in element (5), new projection data is generated in element (12.2b). The model contains information on the geometry and composition of the implant. Correct attenuation coefficients can be derived therefrom which in turn result in correct projection values based on forward projection.

Together with the projections generated from element (11) and the projections produced in element (12.2b), a combination of projection values is generated in element (12.3b). This volume of new projections can bridge the gap in the raw data collection. This allows the reconstruction to draw on a complete data record. When the projections are generated in element (11), the respective metal object information is aligned so that no incorrect information or duplicates result in artificial artefacts.

The following will describe in greater detail a maximum likelihood algorithm for an iterative reconstruction of CT images as an example of a reconstruction method.

The algorithm is based on the assumption that radiation quanta, which are measured by individual detector elements, are governed by a Poisson statistic. The negated log-likelihood function is thereby defined as follows:

$$l(f) = \sum_{i=1}^{M}\left(-n_i\ln(n_0) + n_i\sum_{j=1}^{N}a_{ij}f_j + \ln(n_i!) + n_0\exp\left(-\sum_{j=1}^{N}a_{ij}f_j\right)\right), \quad (1)$$

whereby $n_0$ corresponds to the number of radiation quanta produced at the X-ray tube and $n_i$ corresponds to the measured radiation quanta at detector i, $f \, R^N$ is a vector containing the expected attenuation coefficients and is equatable to the reconstructed image vector. N corresponds to the number of pixels in the image and M the number of detector elements.

By minimizing the function (1), it is possible to reconstruct an image f of the tomographed object from the intensity data n.

It can be determined from further analysis of the equation that the measured intensities $n_i$ whereby i=1 , . . . M and the number $n_0$ of radiation quanta, which are produced at the X-ray tube, are constant for an individual reconstruction problem and do not change over the course of optimization. One therefore does not need to further allow for constant terms in the further analysis of the problem.

The normalized equation with the number of projections M can be depicted in simplified form since the projections caused by metallic bodies responsible for the formation of artefacts should not be included in the reconstruction.

It is further assumed that the attenuation coefficients and the geometry of the metal object (in medicine, e.g. implants or pacemakers) seen in the reconstructed image are known. This prior knowledge can be incorporated into the minimization of a function in the form of an additional constraint. This thus results in an optimization problem which can be formulated as follows: "Minimize the log follicle equation for the reconstruction of CT images under the constraint that certain pixels in the image retain the previously known attenuation coefficients."

The result of this treatment can be depicted in a diagonal matrix which indicates the position and geometry of known metal objects. The further information on the attenuation coefficients of the known metal object is stored as a vector.

The reconstruction method according to the invention is an iterative self-regulating process which preferably utilizes the Augmented Lagrangian approach. A regulating method is thereby used in reconstructing a CT image which establishes a unique solution between an identified minimum and maximum value for the attenuation coefficient up to a predetermined tolerance limit.

A crucial metal artefact reduction step is performed after updating the weighting factors and tolerance limits. If the current tolerance limit falls below a prespecified value and the constraint norm is below a prespecified value, subsequent projections through the known metal object will no longer be disregarded. Instead, new projections will be calculated on the basis of the current iterate and integrated into the acquired data.

Use is hereby made of, for example, a bilateral filter. The objective here is suppressing artefacts in the current iteration and yet preserving edges and structures in the image. Bilateral filters allow softening the image subject to a value range span and a defined number of included neighboring pixels to selectively suppress artefacts. Subsequent the filtering, a forward projection is then used to calculate projection values from this image. The "gap" in the raw data can now be filled and the reconstruction can draw from a complete data record. The quality of the image thereby improves with each iteration and projection data is calculated in each iteration which more faithfully corresponds to the original data and thus ensures fewer artefacts because only acquired projection data through metal, and thus unusable, is replaced.

LIST OF REFERENCE NUMERALS

Elements
1 input and alignment
2 parameterized database
3 data check
4 measurement or data collection
5 generation of metal body data
6 metal body verification
7 masking, filtering, interpolation
8 image reconstruction/generation
9 regulation/termination query
10 filtering
11 generation of projection data
12 combination of data
13 corrected image

What is claimed is:

1. A method for reducing artefacts in computed tomography (CT) images which are caused particularly by obstructive bodies and/or metal bodies, wherein the following sequence of steps is performed in at least one iteration process:

(a) reconstructing or generating CT image data from first projection data;

(b) querying one or more limiting values and/or terminating conditions of the iteration process and, in the case of the limiting values being reached and/or the terminating conditions being met, aborting the iteration process and outputting the CT image data, otherwise continuing the iteration process with step (c);

(c) reducing artefacts in the reconstructed/generated CT image data by filtering the CT image data;

(d) generating second projection data from the filtered CT image data; and (e) combining the first and second projection data, in particular replacing the first projection data with the second projection data in due consideration of obstructive body data and transferring the combined projection data thereby obtained to step (a) as the first projection data.

2. The method for reducing artefacts according to claim 1, wherein the at least one iteration process is integrated into a further process having the following steps:

(f) generating the obstructive body data, particularly obstructive body projection data, on the basis of obstructive body-characterizing parameters stored in a database;

(g) collecting/acquiring first projection data and parameterizing said first projection data;

(h) verifying whether an obstructive body is present in an object based on the first projection data; and (i) processing, in particular masking and/or filtering and/or interpolating the first projection data and transferring the processed first projection data to steps (a) and (f).

3. The method for reducing artefacts according to claim 2, wherein the at least one iteration process is integrated together with the further process into a superordinate process having the following steps:

(j) starting the method;

(k) inputting of data, particularly patient-related data;

(l) retrieving parameters characterizing an obstructive body and/or data identifying the obstructive body from the database on the basis of the entered data; and (m) transferring the retrieved parameters/data to step (f) and/or step (g) and, if applicable, supplementation and/or correction of the parameters/data.

4. The method for reducing artefacts according to claim 1, wherein the at least one iteration process is integrated, in particular together with a further process, into a superordinate process having the following steps:

(f) starting the method;

(g) inputting of data, particularly patient-related data;

(h) retrieving parameters characterizing an obstructive body and/or data identifying an obstructive body from a database on the basis of the entered data; and (i) transferring the retrieved parameters/data to step (a) and, if applicable, supplementation and/or correction of the parameters/data.

5. An apparatus for reducing artefacts in computed tomography (CT) images which are caused particularly by obstructive bodies and/or metal bodies, wherein at least one iterative control loop is configured to perform the following sequence of steps:

(a) reconstructing or generating CT image data from first projection data;

(b) querying one or more limiting values and/or terminating conditions of an iteration process and, in the case of the limiting values being reached and/or the terminating conditions being met, aborting the iteration process and outputting the CT image data, otherwise continuing the iteration process with step (c);

(c) reducing artefacts in the reconstructed/generated CT image data by filtering the CT image data;

(d) generating second projection data from the filtered CT image data; and (e) combining the first and second projection data, in particular replacing the first projection data with the second projection data in due consideration of obstructive body data and transferring the combined projection data thereby obtained to step (a) as the first projection data.

* * * * *